US011505520B2

(12) United States Patent
Bleith et al.

(10) Patent No.: US 11,505,520 B2
(45) Date of Patent: Nov. 22, 2022

(54) METHOD FOR PREPARING KETO-FUNCTIONALIZED AROMATIC (METH)ACRYLATES

(71) Applicant: EVONIK OPERATIONS GMBH, Essen (DE)

(72) Inventors: Tim Bleith, Mainz (DE); Steffen Krill, Mühltal (DE); Thorben Schütz, Alsbach-Hähnlein (DE); Doris Saal, Bensheim (DE); Marcel Treskow, Darmstadt (DE)

(73) Assignee: Evonik Operations GmbH, Essen (DE)

( * ) Notice: Subject to any disclaimer, the term of this patent is extended or adjusted under 35 U.S.C. 154(b) by 0 days.

(21) Appl. No.: 17/057,659

(22) PCT Filed: May 21, 2019

(86) PCT No.: PCT/EP2019/063084
§ 371 (c)(1),
(2) Date: Nov. 21, 2020

(87) PCT Pub. No.: WO2019/224193
PCT Pub. Date: Nov. 28, 2019

(65) Prior Publication Data
US 2021/0214297 A1    Jul. 15, 2021

(30) Foreign Application Priority Data
May 23, 2018    (EP) ..................................... 18173839

(51) Int. Cl.
*C07C 67/08* (2006.01)
*C07C 231/02* (2006.01)
*C08F 220/14* (2006.01)

(52) U.S. Cl.
CPC ............ *C07C 67/08* (2013.01); *C07C 231/02* (2013.01); *C08F 220/14* (2013.01)

(58) Field of Classification Search
None
See application file for complete search history.

(56) References Cited

U.S. PATENT DOCUMENTS

| | | | |
|---|---|---|---|
| 3,642,877 A | 2/1972 | Jayawant | |
| 3,850,988 A * | 11/1974 | Ruby | ........................ C07C 45/81 568/324 |
| 4,215,195 A | 7/1980 | Ponticello et al. | |
| 4,672,105 A | 6/1987 | Schlosser et al. | |
| 4,745,213 A | 5/1988 | Schlosser et al. | |
| 5,395,892 A | 3/1995 | Haeberle et al. | |
| 6,008,404 A | 12/1999 | Miller et al. | |
| 6,706,910 B2 | 3/2004 | Iwakura et al. | |
| 8,420,709 B2 | 4/2013 | Breiner et al. | |
| 8,669,328 B2 | 3/2014 | Breiner et al. | |
| 8,742,163 B2 | 6/2014 | Knebel et al. | |
| 9,512,062 B2 | 12/2016 | Knebel et al. | |
| 9,656,941 B2 | 5/2017 | Kleese et al. | |
| 10,343,980 B2 | 7/2019 | Krill et al. | |
| 10,407,701 B2 | 9/2019 | Kim et al. | |
| 2006/0142408 A1 * | 6/2006 | Liu | ........................ C07C 271/12 522/6 |
| 2011/0196169 A1 * | 8/2011 | Knebel | .................... C07C 67/08 560/140 |
| 2011/0218312 A1 | 9/2011 | Knebel et al. | |
| 2014/0288330 A1 | 9/2014 | Broell et al. | |
| 2016/0297738 A1 * | 10/2016 | Klesse | ..................... B01J 31/04 |
| 2019/0352251 A1 | 11/2019 | Hartmann | |
| 2020/0331845 A1 | 10/2020 | Treskow | |
| 2021/0163439 A1 | 6/2021 | Treskow et al. | |
| 2021/0179529 A1 | 6/2021 | Treskow et al. | |
| 2021/0179531 A1 | 6/2021 | Treskow et al. | |
| 2021/0269393 A1 | 9/2021 | Treskow et al. | |
| 2021/0332005 A1 | 10/2021 | Treskow et al. | |
| 2022/0056005 A9 | 2/2022 | Treskow et al. | |
| 2022/0112154 A1 | 4/2022 | Treskow et al. | |

FOREIGN PATENT DOCUMENTS

| | | | | |
|---|---|---|---|---|
| CA | | 1340884 | 1/2000 | |
| EA | | 201501099 | 7/2016 | |
| EP | | 0016518 | 10/1980 | |
| EP | | 2246403 | 11/2010 | |
| GB | | 1193412 | 6/1970 | |
| GB | | 2 162 516 | 2/1986 | |
| GB | | 2248234 | 4/1992 | |
| JP | | 2003261506 | 9/2003 | |
| SU | | 234254 | 1/1969 | |
| TW | | 201807491 | 3/2018 | |
| WO | WO 2009/146995 | | 12/2009 | |
| WO | WO 2010/021956 | | 2/2010 | |
| WO | WO-2015049200 A1 * | | 4/2015 | ............. C07C 67/08 |
| WO | WO 2017/145022 | | 8/2017 | |

(Continued)

OTHER PUBLICATIONS

International Search Report for corresponding international application PCT/EP2019/063084, filed May 21, 2019.
Written Opinion of the International Searching Autjority for corresponding international application PCT/EP2019/063084, filed May 21, 2019.
European Search Report Search Opinion for corresponding European application EP 18 17 3839 filed May 23, 2019 with English language machine translation of the Search Opinion attached.
Casas, et al., "Kinetics of chemical interesterification of sunflower oil with methyl acetate for biodiesel and triacetin production," *Chemical Engineering Journal* 171:1324-1332 (2011).
U.S. Appl. No. 16/753,287, filed Apr. 2, 2020, US-2020/0331845 A1, Oct. 22, 2020, Treskow.

(Continued)

*Primary Examiner* — Amy C Bonaparte
(74) *Attorney, Agent, or Firm* — Law Office of Michael A. Sanzo, LLC

(57) ABSTRACT

The invention relates to a method for preparing keto-functionalized aromatic (meth)acrylates.

22 Claims, No Drawings

(56) References Cited

FOREIGN PATENT DOCUMENTS

| WO | WO 2017/147040 | 8/2017 |
| WO | WO 2012/084737 | 6/2021 |

OTHER PUBLICATIONS

U.S. Appl. No. 16/479,497, filed Jul. 19, 2019, US-2019/0352251 A1, Nov. 21, 2019, Hartman.
U.S. Appl. No. 16/973,995, filed Dec. 10, 2020, Treskow.
International Preliminary Report on Patentability for corresponding international application PCT/EP2019/063084, filed May 21, 2019.
O' Donnell, et al., "Microstructure, Kinetics, and Transport in Oil-in-Water Microemulsion Polymerizations," *Macromolecular Rapid Communications* 28(14):1445-1454 (2007).
U.S. Appl. No. 17/260,223, filed Jan. 14, 2021, Treskow.
U.S. Appl. No. 17/260,226, filed Jan. 14, 2021, Treskow.
U.S. Appl. No. 17/262,735, filed Jan. 14, 2021, Treskow.
U.S. Appl. No. 17/268,463, filed Feb. 13, 2021, Treskow.
U.S. Appl. No. 17/268,465, filed Feb. 13, 2021, Treskow.
Airgas: Methylamines (downloaded on Mar. 8, 2022 from https://web.archive.org/web/20160302072912/http://airgasspecialtyproducts.com/products/methylamines/; originally captured by the Wayback Machine on Mar. 2, 2016).

\* cited by examiner

METHOD FOR PREPARING KETO-FUNCTIONALIZED AROMATIC (METH)ACRYLATES

CROSS REFERENCE TO RELATED APPLICATIONS

The present application is US national stage of international application PCT/EP2019/063084, which had an international filing date of May 21, 2019, and which was published on Nov. 28, 2019. The PCT application claims priority to European application EP 18173839.4, filed on May 23, 2018. The contents of each of these applications is hereby incorporated by reference in its entirety.

The invention relates to a method for preparing keto-functionalized aromatic (meth)acrylates.

The prior art contains a method for preparing [(meth)acryloyloxy]benzophenone starting from (meth)acrylic anhydride (JP2003261506, Mitsubishi Rayon). Triethylamine is used as catalyst and reagent. Since the amine forms a salt with the methacrylic acid produced during the reaction, the amine must be made equimolar with the hydroxybenzophenone. Correspondingly, equimolar amounts of salt are obtained, and have to be disposed of as waste. The economics of the process are therefore poor. In addition, the work is carried out at very moderate temperatures (30° C.), which, despite high catalyst amounts, leads to long reaction times of >5 h. Thus, the method is also disadvantageous taking into account the space-time yield.

In a more recent application WO2017/146444, an enzymatic reaction of (meth)acrylic esters (e.g. vinyl acrylate) with 4-hydroxybenzophenone is described. The reaction takes place at moderate temperatures around 60° C., the reaction times are 8 h. For isolation, drying is carried out for several days at 50° C. Thus, reaction times and the expenditure for isolation are uneconomical. The high yields achievable and high product purity are mentioned to justify the excessive expenditure.

In WO 2017/147040, the reaction in a microflow reactor between 4-hydroxybenzophenone and methacryloyl chloride in the presence of superstoichiometric amounts of triethylamine is described. The amounts of salt formed, which must be removed or reworked, make the method uneconomical and expensive.

Other methods in the prior art are the reaction of (meth)acryloyl chloride with hydroxy-functional benzophenones, and the reaction of this raw material with glycidyl methacrylate. When handling (meth)acryloyl chloride, the corrosive and caustic properties must be borne in mind and in addition stoichiometric amounts of a base, for example triethylamine, are always used. This makes such a method very expensive. The use of glycidyl methacrylate is disadvantageous on account of the high toxicity.

WO2010/072479 describes the preparation of [(meth)acryloyloxy]benzophenone in the presence of catalytic amounts of sulfuric acid. When reaction is at an end, the catalyst has to be neutralized with aqueous sodium hydroxide solution, and removed by filtration as sodium sulfate. While this method is technically feasible, the long residence times of 4-8 hours however mean that the space-time yields are not advantageous. Despite the long residence time, the hydroxybenzophenone conversions are incomplete, which is disadvantageous for the subsequent use in the form of a polymer, e.g. as additive for paints and dyes. As is known, residual monomers and other molecules which are not covalently incorporated into the polymer migrate over the lifetime of the application and can thus be released into the environment, which is undesirable. No mention is made of further by-products which cannot be bonded as monomer in a polymer.

WO2015/049200 describes a method for preparing [(meth)acryloyloxy]benzophenone in the presence of catalytic amounts of basic salts. In this case, long residence times, customarily of 5 h at 90° C., are required for the reaction. In addition, the method described therein requires high concentrations of stabilizer of more than 2600 ppm Topanol A (based on 4-hydroxybenzophenone), which entails a high concentration of stabilizer of more than 800 ppm in the product. Here, the by-products of the reaction are also quantified, namely unreacted 4-hydroxybenzophenone and 4-acetoxybenzophenone, which are of the order of magnitude of a few percent in each case relative to the target products, and which remain in the product. In terms of space-time yields, and also the product quality which can be achieved, this method is therefore not optimal.

DE 1720603 describes a method for preparing aqueous dispersions of readily crosslinkable polymers. This involves copolymerizing acrylic and methacrylic esters with photoactive, olefinically unsaturated monomers, with optional accompanying use of photoactive, nonionic emulsifiers.

EP0346788 describes a method for preparing radiation-sensitive carbamoylbenzo- and -acetophenones having at least one methacrylate or acrylate end group. This involves reacting isocyanatoalkyl (meth)acrylates with hydroxyacetophenones or hydroxybenzophenones, using a basic catalyst. It is necessary here to operate in the absence of moisture. Moreover, only dried, non-nucleophilic solvents can be used.

It was an object to provide an improved method for preparing keto-functionalized aromatic (meth)acrylates.

The object was achieved by a method for the preparation of keto-functionalized aromatic (meth)acrylates by reacting keto-functionalized aromatic alcohols or keto-functionalized aromatic amines and (meth)acrylic anhydride, in which reactants, products and catalyst are present together in the reaction matrix at a reaction temperature between 50° C. and 120° C., characterized in that the residence time of the reactants, products and catalysts is restricted from 0.1 to at most 4 hours and (meth)acrylic anhydride is used at a content of (meth)acrylic acetic anhydride of <4.5%.

Surprisingly, it has been found that high conversions are achieved, and the amount of by-products is greatly reduced, with the method according to the invention.

It has been found that the inventive method is only burdened with a small salt load, which was either used as catalyst or is formed when the catalyst acid is neutralized during work-up. The (meth)acrylic acid generated as a by-product can be used in the subsequent polymerization of the keto-functionalized aromatic (meth)acrylate monomers as comonomer or can be recycled for preparing new (meth)acrylic anhydride.

Keto-Functionalized Aromatic (Meth)Acrylates
Keto-Functionalized Aromatic (Meth)Acrylates

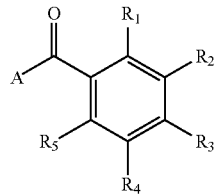

A=alkyl, aryl, heteroaryl, substituted with any desired selection from H, alkyl, aryl, halides, OAlkyl, NO₂, OH, sulfonyl, NH₂, NAlkyl₂

R₁, R₂, R₃, R₄, R₅=different or identical to one another, selected from H, alkyl, halide, OAlkyl, NO₂, OH, sulfonyl, NH₂, NAlkyl₂ with a ring closure also being explicitly included between A and one of the radicals R₁₋₅, e.g. as fluorenone derivative with one of the substituents R₁₋₅ being described by the following formula

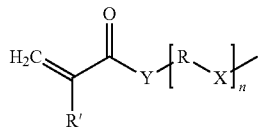

n=0-10, preferably n=1-6
R=alkyl, aryl, oligoether, CO
R'=H, Me
X=O, S, NH
Y=O, NH Preferred:
Keto-Functionalized Aromatic (Meth)Acrylates

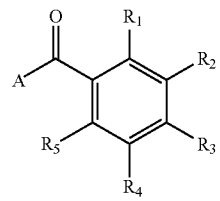

A=alkyl, aryl, heteroaryl, substituted with any desired selection from H, alkyl, aryl, halides, OAlkyl, NO₂, OH, sulfonyl, NH₂, NAlkyl₂

R₁, R₂, R₃, R₄, R₅=different or identical to one another, selected from H, alkyl, halide, OAlkyl, NO₂, OH, sulfonyl, NH₂, NAlkyl₂ with a ring closure also being explicitly included between A and one of the radicals R₁₋₅, e.g. as fluorenone derivative with one of the substituents R₁₋₅ being described by the following formula

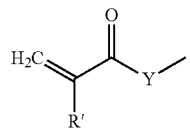

R'=H, Me
Y=O, NH

More Preferred:
Keto-Functionalized Aromatic (Meth)Acrylates

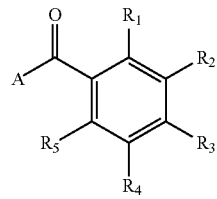

A=alkyl, aryl, heteroaryl, substituted with any desired selection from H, alkyl, aryl, halides, OAlkyl, NO₂, OH, sulfonyl, NH₂, NAlkyl₂

R₁, R₂, R₃, R₄, R₅=different or identical to one another, selected from H, alkyl, halide, OAlkyl, NO₂, OH, sulfonyl, NH₂, NAlkyl₂ with one of the substituents R₁₋₅ being described by the following formula

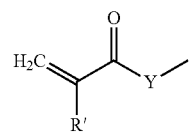

R'=H, Me
Y=O, NH

Furthermore Preferred:
Keto-Functionalized Aromatic (Meth)Acrylates

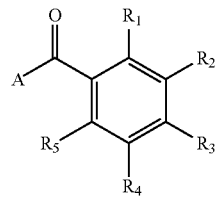

A=alkyl, aryl, substituted with any desired selection from H, alkyl, aryl, halides, OAlkyl, NO₂, OH, sulfonyl, NH₂, NAlkyl₂

R₁, R₂, R₃, R₄, R₅=different or identical to one another, selected from H, alkyl, halide, OAlkyl, NO₂, OH, sulfonyl, NH₂, NAlkyl₂ with one of the substituents R₁₋₅ being described by the following formula

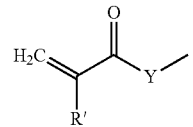

R'=H, Me
Y=O, NH

Particularly Preferred:
Keto-Functionalized Aromatic (Meth)Acrylates

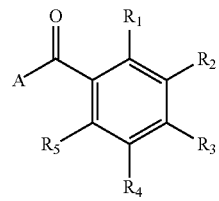

A=aryl, substituted with any desired selection from H, alkyl, aryl, halides, OAlkyl, $NO_2$, OH, sulfonyl, $NH_2$, $NAlkyl_2$ $R_1$, $R_2$, $R_3$, $R_4$, $R_5$=different or identical to one another, selected from H, alkyl, halide, OAlkyl, $NO_2$, OH, sulfonyl, $NH_2$, $NAlkyl_2$ with one of the substituents $R_1$-5 being described by the following formula

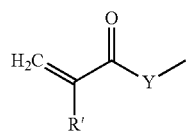

R'=H, Me
Y=O, NH

Most Particularly Preferred:
Keto-Functionalized Aromatic (Meth)Acrylates

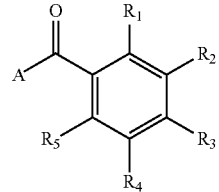

A=aryl, substituted with any desired selection from H, alkyl, halides, OAlkyl, sulfonyl, $NAlkyl_2$ $R_1$, $R_2$, $R_3$, $R_4$, $R_5$=different or identical to one another, selected from H, alkyl, halide, OAlkyl, sulfonyl, $NAlkyl_2$ with one of the substituents $R_{1-5}$ being described by the following formula

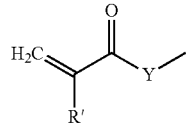

R'=H, Me
Y=O, NH

Especially Preferred:
Keto-Functionalized Aromatic (Meth)Acrylates

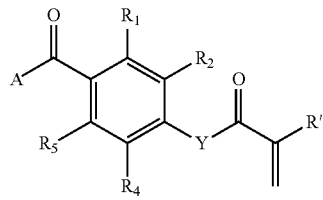

A=aryl, substituted with any desired selection from H, alkyl, halides, OAlkyl, sulfonyl, $NAlkyl_2$ $R_1$, $R_2$, $R_3$, $R_4$=different or identical to one another, selected from H, alkyl, halide, OAlkyl, sulfonyl, $NAlkyl_2$ R'=H, Me
Y=O, NH Exemplary, Non-Limiting Representatives of Keto-Functionalized Aromatic (Meth)Acrylates

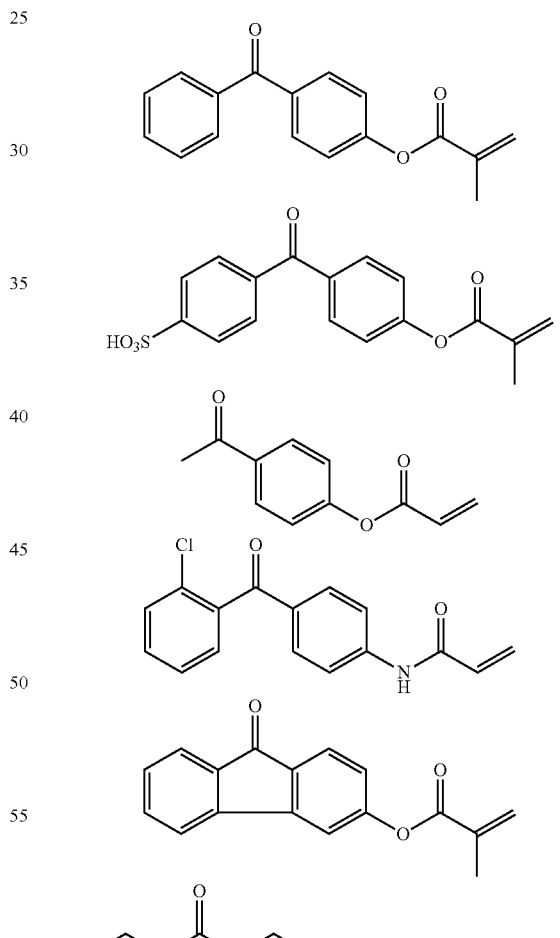

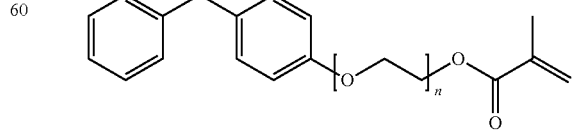

n = 1-10

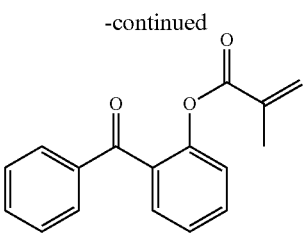

The notation "(meth)acrylate" here means both methacrylate, for example methyl methacrylate, ethyl methacrylate, etc., and acrylate, for example methyl acrylate, ethyl acrylate, etc., and mixtures of the two.

Keto-Functionalized Aromatic Alcohols and Keto-Functionalized Aromatic Amines

The keto-functionalized aromatic alcohols or keto-functionalized aromatic amines used are characterized in that they have a keto function directly adjacent to an aromatic system and additionally have either an $NH_2$ or OH group on the aromatic system (phenylamine/aniline; phenylalcohol/phenol) or a spacer with a free $NH_2$ or OH group (e.g. benzylamine, benzylalcohol). The spacer unit may be or comprise oligoethers, alkyl-, aryl-, -ethers, -thioethers-amines, -esters, -thioesters, or -amides. Preference is given to keto-functionalized aromatic alcohols or amines which have an $NH_2$ or OH group on the aromatic system. Furthermore, preference is given to derivatives in which the two substituents of the keto function are not directly connected to one another. Moreover, preference is given to those keto-functionalized aromatic alcohols or amines which do not contain any heteroatoms. Particularly preferred representatives of the keto-functionalized aromatic alcohols or amines are benzophenone derivatives, most particularly preferably benzophenone derivatives which are substituted with H, alkyl, halide, alkoxy, sulfonyl or dialkylamine groups. Preference is especially given here to benzophenone derivatives, the $NH_2$ or OH function of which is in the para position relative to the keto function. Most particularly preferred keto-functionalized alcohols or amines are represented by the corresponding compounds which, according to the inventive reaction, lead to the inventive keto-functionalized aromatic (meth)acrylates. The keto-functionalized aromatic alcohols or amines are usually characterized by a purity of >96%. This degree of purity can contribute to achieving a low colour index in the product.

Catalyst

The reaction of keto-functionalized aromatic alcohols or keto-functionalized aromatic amines and (meth)acrylic anhydride can take place in the presence of acids, preferably customary strong inorganic or organic acids having a $pK_a$ value of <2 and particularly preferably in the presence of sulfuric acid or alkyl- or arylsulfonic acids. Alternatively, bases have also proved to be suitable catalysts. Preferred bases in this case are carboxylate salts or else stronger bases having a $pK_b$ value of <9, for example sodium hydroxide, sodium methoxide or potassium hydroxide and mixtures thereof, since these generate the corresponding (meth)acrylate salt in situ by reaction with (meth)acrylic anhydride.

Preferably, the reaction is carried out in the presence of catalytic amounts of concentrated sulfuric acid or aqueous sodium hydroxide solution. The catalytic amounts are preferably between 0.01 and 3 mol % based on the (meth)acrylic anhydride used and particularly preferably between 0.2 and 1.5 mol % based on the (meth)acrylic anhydride used.

Stabilizer

Suitable stabilizers are known to those skilled in the art. They include, for example, phenothiazine, substances having an oxyl radical, such as 2,2,6,6-tetramethylpiperidinyl-N-oxyl (TEMPO), 4-hydroxy-2,2,6,6-tetramethylpiperidinyl-N-oxyl (TEMPOL) or 4-(meth)acryloyloxy-2,2,6,6-tetramethylpiperidinyl-N-oxyl (TEMPOL-(meth)acrylate) and also phenol derivatives such as hydroquinone monomethyl ether (HQME), 2,4-dimethyl-6-tert-butylphenol (DMBP), 2,6-di-tert-butylphenol or 4-methyl-2,6-di-tert-butylphenol (BHT). Mixtures of different stabilizers can also be used. Preference is given to using sterically hindered phenols; particular preference is given to using HQME, DMBP, BHT and also mixtures of these substances. The applications of keto-functionalized aromatic (meth)acrylates generally require colourless products. Therefore, for unsaturated compounds, preference is given to non-colouring stabilizers or colouring stabilizers in very small amounts. The amount used of stabilizer is dependent on the starting materials. The amount of stabilizer at the start of the reaction is adjusted to be between 0 and 5000 ppm based on the keto-functionalized aromatic alcohols or amines used. Preferably, the amount of stabilizer at the start of the reaction is adjusted to be between 0 and 3000 ppm based on the keto-functionalized aromatic alcohols or amines used, particularly preferably between 50 and 2000 ppm.

(Meth)Acrylic Anhydride

The (meth)acrylic anhydride is added in a small excess to the keto-functionalized aromatic alcohols or amines. In this case, a molar ratio of alcohol or amine to (meth)acrylic anhydride of 1:1.01 to 1:4, preferably between 1:1.03 to 1:2, particularly preferably between 1:1.05 to 1:1.5 is chosen. The (meth)acrylic anhydride is used with a purity of >93%, preferably >94%, particularly preferably >96%, most particularly preferably >98%.

Both acetoxy derivative and remaining alcohol or amine are not reacted in the radical polymerization and are therefore present in the polymer in unbound form. These substances can migrate and are therefore detrimental to the adjustment of the properties of the polymer. In addition, toxic substances may potentially be released into the environment in this way. Therefore, a high conversion of the alcohol or amine used is critical. As a result, the above purity requirement is directly applicable to the (meth)acrylic anhydride. The acetoxy derivative in turn originates from the mixed anhydride of (meth)acrylic acid and acetic acid, which is a typical impurity of (meth)acrylic anhydride. This species preferably transfers the acetyl radical. In order to limit the content of acetoxy derivative in the product, the (meth)acrylic anhydride used must have a content of mixed anhydride of (meth)acrylic acid and acetic acid, hereinafter referred to as (meth)acrylic acetic anhydride, of <4.5 wt %, preferably <3 wt %, particularly preferably <1.5 wt %.

Reaction Conditions

The reaction is carried out at temperatures between 50° C. and 120° C., preferably 60° C. to 95° C., particularly preferably between 70° C. and 90° C., with a residence time of 0.1 to 4 hours, preferably of 1 to 3 hours.

In order to avoid the formation of undesired by-products, the reaction is interrupted at a conversion of >90%, preferably >95%, particularly preferably >97% of the reactant used.

Neutralization and Work-Up

In the case of acids being used catalytically, the neutralization is carried out with aqueous bases, preferably with aqueous alkali metal hydroxide solution or ammonia solution. Basic catalysts do not have to be neutralized. By treating the catalyst, in the simplest case a neutralization, a colour change may arise.

The keto-functionalized aromatic (meth)acrylates prepared in high purity can be directly dissolved from the crude product in customary organic solvents, (meth)acrylic esters, preferably methyl methacrylate, n-butyl methacrylate, isobutyl methacrylate and/or styrene and also subsequently stored and further reacted.

Preference is given to a mixture of 10-50 wt % of the keto-functionalized aromatic (meth)acrylate in 30-80 wt % of methyl methacrylate in the presence of <15 wt % of (meth)acrylic acid; particular preference is given to a mixture of 25-35 wt % of the keto-functionalized aromatic (meth)acrylate in 55-65 wt % of methyl methacrylate in the presence of 8-12 wt % of (meth)acrylic acid.

The subsequent work-up of the crude monomer may be carried out by adding water. In this case, the keto-functionalized aromatic (meth)acrylate precipitates by addition of excess water and is isolated in solid form by filtration. It is just as possible to introduce the crude monomer into water. In this way, the (meth)acrylic acid forming in the course of the reaction, the catalyst and the salts from the neutralization thereof, and other water-soluble impurities, are separated off. In accordance with expectations, however, a significant depletion of the unreacted reactant or the acetylated by-product is not achieved in this way, which emphasizes the fact that, in order to obtain a particularly pure product, a (meth)acrylic anhydride with as low as possible a content of mixed anhydride of (meth)acrylic acid and acetic acid must be used.

An alternative work-up of the crude monomer can be carried out by addition of organic solvents to the crude product at elevated temperatures, for example between 60 and 100° C. The crude monomer can also be added to an organic solvent with the same result. Possible solvents are organic esters, for example methyl methacrylate or butyl acetate, linear or cyclic alkanes, preferably methylcyclohexane, or aromatic compounds, preferably toluene. In this case, the keto-functionalized aromatic (meth)acrylate is firstly dissolved and precipitates upon subsequent cooling to room temperature. The target product is isolated in solid form by filtration. The methacrylic acid and also the catalyst or salts from the neutralization thereof are separated off in this way. In addition, a slight depletion in the by-product 4-(acetoxy)benzophenone is observed.

Also proceeding from the worked-up pure product, corresponding solutions can be prepared in customary organic solvents, (meth)acrylic esters, preferably methyl methacrylate, n-butyl methacrylate, isobutyl methacrylate and/or styrene.

Preferred Method Variants

1. Method for the preparation of keto-functionalized aromatic (meth)acrylates by reacting keto-functionalized aromatic alcohols or amines and (meth)acrylic anhydride, in which reactants, products and catalyst are present together in the reaction matrix at a reaction temperature between 50° C. and 120° C., characterized in that the residence time of the reactants, products and catalysts is restricted from 0.1 to at most 4 hours, (meth)acrylic anhydride is used at a content of (meth)acrylic acetic anhydride of <4.5%, the amount of stabilizer at the start of the reaction is adjusted to be between 0 and 5000 ppm based on the keto-functionalized aromatic alcohols or amines used, and (meth)acrylic anhydride is used with a purity of >93%.

2. Method for the preparation of keto-functionalized aromatic (meth)acrylates by reacting keto-functionalized aromatic alcohols or aminess and (meth)acrylic anhydride, in which reactants, products and catalyst are present together in the reaction matrix at a reaction temperature between 50° C. and 120° C., characterized in that the residence time of the reactants, products and catalysts is restricted from 0.1 to at most 4 hours, (meth)acrylic anhydride is used at a content of (meth)acrylic acetic anhydride of <4.5%, the amount of stabilizer at the start of the reaction is adjusted to be between 0 and 5000 ppm based on the keto-functionalized aromatic alcohols or amines used, and the reaction is interrupted at a conversion of >90% of the reactant used.

3. Method for the preparation of keto-functionalized aromatic (meth)acrylates by reacting keto-functionalized aromatic alcohols or amines and (meth)acrylic anhydride, in which reactants, products and catalyst are present together in the reaction matrix at a reaction temperature between 50° C. and 120° C., characterized in that the residence time of the reactants, products and catalysts is restricted from 0.1 to at most 4 hours, (meth)acrylic anhydride is used at a content of (meth)acrylic acetic anhydride of <4.5%, the amount of stabilizer at the start of the reaction is adjusted to be between 0 and 5000 ppm based on the keto-functionalized aromatic alcohols or amines used, and the reaction is carried out in the presence of catalytic amounts of acid.

4. Method for the preparation of keto-functionalized aromatic (meth)acrylates by reacting keto-functionalized aromatic alcohols or amines and (meth)acrylic anhydride, in which reactants, products and catalyst are present together in the reaction matrix at a reaction temperature between 50° C. and 120° C., characterized in that the residence time of the reactants, products and catalysts is restricted from 0.1 to at most 4 hours, (meth)acrylic anhydride is used at a content of (meth)acrylic acetic anhydride of <4.5%, the amount of stabilizer at the start of the reaction is adjusted to be between 0 and 5000 ppm based on the keto-functionalized aromatic alcohols or amines used, and the keto-functionalized aromatic (meth)acrylate precipitates by addition of water or of an organic solvent into the reaction mixture and is isolated in solid form by filtration.

5. Method for the preparation of keto-functionalized aromatic (meth)acrylates by reacting keto-functionalized aromatic alcohols or amines and (meth)acrylic anhydride, in which reactants, products and catalyst are present together in the reaction matrix at a reaction temperature between 50° C. and 120° C., characterized in that the residence time of the reactants, products and catalysts is restricted from 0.1 to at most 4 hours, (meth)acrylic anhydride is used at a content of (meth)acrylic acetic anhydride of <4.5%, the amount of stabilizer at the start of the reaction is adjusted to be between 0 and 5000 ppm based on the keto-functionalized aromatic alcohols or amines used, and the keto-functionalized aromatic (meth)acrylate is prepared by addition of a liquid (meth)acrylic ester or styrene into the product mixture as solution in said ester or in styrene.

In the application for coatings and paints, the Hazen colour index (also known as Pt—Co colour index) of the raw materials used is of critical importance. The colour index of the products described here can be reduced by using adsorbents, preferably activated carbon. Suitable in principle are different adsorbents which reduce the Pt—Co colour index after the reaction is carried out; these adsorbents are added to the crude mixture as slurry and are later removed again or, in an alternative embodiment, operate as fixed bed. Thus, when using 10 wt % of activated carbon, a reduction of the colour index by approximately 100 APHA is achieved within less than 2 h. Since the activated carbon cannot be directly reused, such a method is very expensive. It is therefore advantageous to keep the colour index low even during the reaction, such that further work-up is not required. To this end, the method steps according to Claims 1-3 and 5-13 of the inventive method are preferably combined such that the Pt—Co colour index of a 30 wt % solution of the reaction product, after neutralization of the catalyst with a base in 60 wt % MMA and 10 wt % methacrylic acid, is adjusted to <500 APHA, preferably to <400 APHA, particularly preferably to <350 APHA.

Keto-functionalized aromatic (meth)acrylates can, for subsequent photocrosslinking of polymers by daylight or UV light, also be used as polymeric photoinitiators (as described in WO2010112474A1 and the references cited therein).

The keto-functionalized aromatic (meth)acrylates can additionally be used as comonomer for polymerization reactions.

The examples given below better illustrate the present invention, without however restricting the invention to the features disclosed therein.

EXAMPLES

Abbreviations Used

4-HBP 4-hydroxybenzophenone
BpMA 4-(methacryloyloxy)benzophenone
GC Gas chromatography
MAAH methacrylic anhydride
MAA methacrylic acid
MMA methyl methacrylate

Example 1

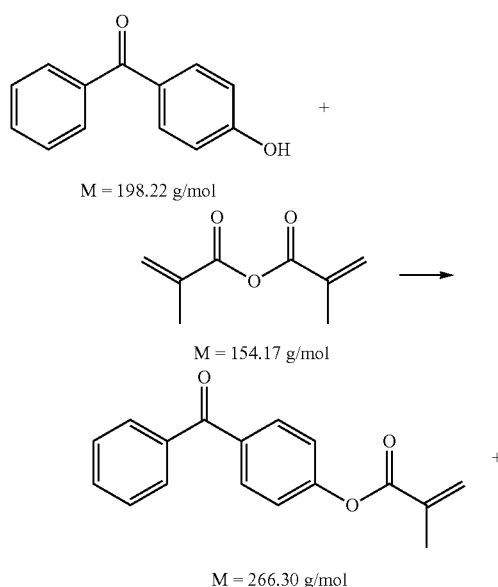

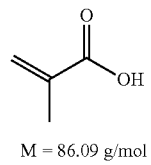

M = 86.09 g/mol

Apparatus: 2 l four-necked round-bottom flask with mechanical stirrer, reflux condenser, Pt100 temperature sensor, air inlet tube and electrically heated oil bath.

Mixture:
1.51 mol of 4-hydroxybenzophenone, 99.8%: 300 g
1.70 mol of MAAH (purity 98.48% (GC), methacrylic acetic anhydride 1.131%,
acetic anhydride not detected;
stabilized with 1871 ppm of 2,4-dimethyl-6-tert-butylphenol): 262.8 g
1.80 mol of MMA: 180 g
0.0087 mol of concentrated sulfuric acid: 0.846 g
Total stabilizer content at start of reaction: 1639 ppm based on 4-hydroxybenzophenone.
Neutralization of the catalyst acid with 1.57 g of (50% strength) aqueous sodium hydroxide solution Esterification of the excess methacrylic anhydride with 9.7 g of methanol (0.3 mol)
For the preparation of the 30% strength solution in MMA: 600 g MMA
Theoretical yield: 1354 g Procedure:

The mixture was weighed out in full and then heated to 90° C. with stirring and introduction of air. The reaction time at 90° C. is 3 h. Cooling was then carried out, down to approximately 60° C., and the sodium hydroxide dissolved in water for neutralization of the catalyst sulfuric acid, and also the methanol for esterification of the unreacted methacrylic anhydride, were added. Here, the colour of the reaction mixture changed from red to yellow. Stirring was subsequently carried out for 1 h at 60° C., and then 600 g of methyl methacrylate were added to the mixture with stirring. The resulting solution was cooled to room temperature with stirring, and filtered. The solution of the 4-(methacryloyloxy)benzophenone in methyl methacrylate has the following composition, determined by gas chromatography (figures in wt %):

57.8% methyl methacrylate
10.0% methacrylic acid
0.30% 4-hydroxybenzophenone
0.62% 4-(acetoxy)benzophenone
29.4% 4-(methacryloyloxy)benzophenone The water content is 0.09%, the stabilizer content is 22 ppm of 2,4-dimethyl-6-tert-butylphenol. The Pt—Co colour index is 194 APHA.

During the reaction, samples were taken and worked up separately (cooling to 60° C., neutralization with aqueous sodium hydroxide solution, reaction with MeOH, dilution with MMA). The conversion was determined by comparison of the 4-HBP signal with the starting value by means of GC.

|  | Conversion 4-HBP | Colour index [APHA] after work-up | Content of the stabilizer used after work-up [ppm] |
| --- | --- | --- | --- |
| Reaching 90° C. | 89.6% | 146 | 173 |
| 15 min | 95.2% | | |

| | Conversion 4-HBP | Colour index [APHA] after work-up | Content of the stabilizer used after work-up [ppm] |
|---|---|---|---|
| 30 min | 96.6% | | |
| 45 min | 97.1% | | |
| 60 min | 97.6% | 140 | 130 |
| 75 min | 97.4% | | |
| 90 min | 97.4% | | |
| 120 min | 97.5% | 157 | 82 |
| 180 min | 98.0% | 198 | 23 |

Yield: 1285 g (95% of theory)

Example 2

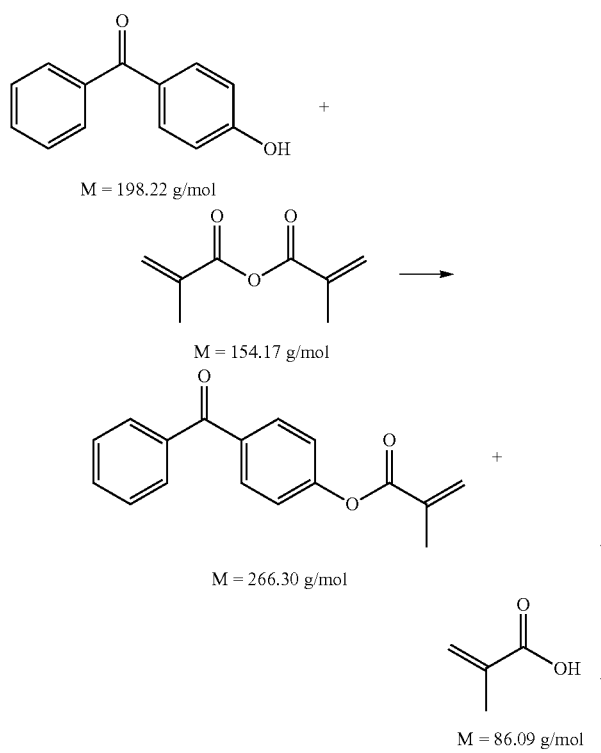

Apparatus: 2 l four-necked round-bottom flask with mechanical stirrer, reflux condenser, Pt100 temperature sensor, air inlet tube and electrically heated oil bath.

Mixture:

1.51 mol of 4-hydroxybenzophenone, 99.7%: 300 g 1.70 mol of MAAH (purity 98.59% (GC), methacrylic acetic anhydride 0.40%,
  acetic anhydride not detected;
  stabilized with 2070 ppm of 2,4-dimethyl-6-tert-butylphenol): 262.8 g 1.80 mol of MMA: 180 g 0.0087 mol of concentrated sulfuric acid: 0.846 g Total stabilizer content at start of reaction: 1813 ppm based on 4-hydroxybenzophenone.

Neutralization of the catalyst acid with 1.8 g of aqueous sodium hydroxide solution dissolved in 10 g of water Esterification of the excess methacrylic anhydride with 22.4 g of methanol Theoretical yield: 1354 g Procedure:

The mixture was weighed out in full and then heated to 90° C. with stirring and introduction of air. The reaction time at 90° C. is 2 h. Cooling was then carried out, down to approximately 60° C., and the sodium hydroxide dissolved in water for neutralization of the catalyst sulfuric acid, and also the methanol for esterification of the unreacted methacrylic anhydride, were added. Stirring was subsequently carried out for 1 h at 60° C., and then 600 g of methyl methacrylate were added to the mixture with stirring. The resulting solution was cooled to room temperature with stirring, and filtered. The solution of 4-(methacryloyloxy)benzophenone in methyl methacrylate has the following composition, determined by gas chromatography (figures in wt %):

57.9% methyl methacrylate
10.0% methacrylic acid
0.28% 4-hydroxybenzophenone
0.32% 4-(acetoxy)benzophenone
29.8% 4-(methacryloyloxy)benzophenone The water content is 0.08%, the stabilizer content is 53 ppm of 2,4-dimethyl-6-tert-butylphenol. The Pt—Co colour index is 152 APHA.

Direct comparison with example 1 shows that the starting concentration of methacrylic acetic anhydride in the methacrylic anhydride is critical for the amount of 4-(acetoxy)benzophenone found in the product.

Yield: 1350 g (99.7% of theory)

Example 3

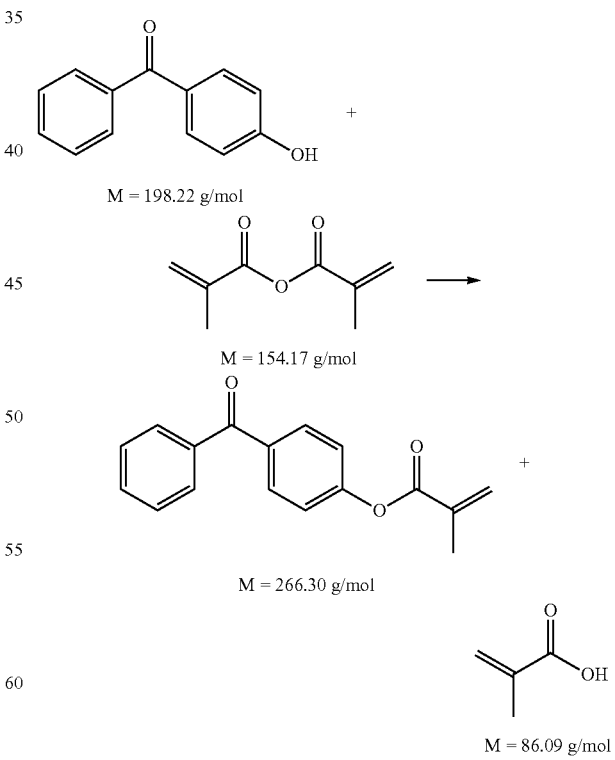

Apparatus: 2 l four-necked round-bottom flask with mechanical stirrer, reflux condenser, Pt100 temperature sensor, air inlet tube and electrically heated oil bath.

Mixture:
1.51 mol of 4-hydroxybenzophenone, 99.7%: 300 g
1.70 mol of MAAH (purity 98.59% (GC), methacrylic acetic anhydride 0.40%,
  acetic anhydride not detected;
    stabilized with 2070 ppm of 2,4-dimethyl-6-tert-butylphenol): 262.8 g
1.80 mol of MMA: 180 g
0.0087 mol of concentrated sulfuric acid: 0.846 g
Total stabilizer content at start of reaction: 1813 ppm based on 4-hydroxybenzophenone.
Neutralization of the catalyst acid with 1.8 g of aqueous sodium hydroxide solution dissolved in 10 g of water
Esterification of the excess methacrylic anhydride with 22.4 g of methanol
Theoretical yield: 402.1 g
Procedure:
The mixture was weighed out in full and then heated to 90° C. with stirring and introduction of air. The reaction time at 90° C. is 2 h. Cooling was then carried out, down to approximately 60° C., and the sodium hydroxide dissolved in water for neutralization of the catalyst sulfuric acid, and also the methanol for esterification of the unreacted methacrylic anhydride, were added. Stirring was subsequently carried out for 1 h at 60° C., then the mixture was poured with stirring (metal paddle stirrer, stirring motor) as a thin stream into 1.5 l of water. After 0.5 h of stirring, the precipitate was isolated by suction filtration on a glass filter frit, washed twice again with in each case 1 l of water and subsequently dried using air on the suction filter. The solid was subsequently dried in air.
Yield: 397.2 g (98.8% of theory)
Analyses: Water content: 0.10%
2,4-dimethyl-6-tert-butylphenol: 120 ppm
Gas Chromatography:
0.059% methyl methacrylate
0.011% methacrylic acid
0.659% 4-hydroxybenzophenone
0.723% 4-(acetoxy)benzophenone
98.23% 4-(methacryloyloxy)benzophenone
Pt—Co colour index as 20% strength solution in acetone: 135.

Direct comparison with example 2 shows that the contents of 4-hydroxybenzophenone and 4-(acetoxy)benzophenone are not significantly reduced by the precipitation. This highlights the importance of a (meth)acrylic anhydride with as low a content of (meth)acrylic acetic anhydride as possible for a pure product.

Example 4

Apparatus: 2 l round-bottom flask with mechanical stirrer and reflux condenser.
Mixture:
1 kg of the following solution:
30% of 4-(methacryloyloxy)benzophenone dissolved in 60% methyl methacrylate and 10% methacrylic acid directly from the process analogous to example 1, but with a higher colour index.
100 g of activated carbon rods (from Donau Carbon, Norit 0.8 Supra type)
Procedure:
The mixture was weighed out in full and stirred at room temperature. In the meantime, samples were taken continuously and were filtered by a pleated filter and a syringe filter (PTFE, pore size 0.45 µm).

| Time | Pt—Co colour index |
| --- | --- |
| Beforehand | 335 |
| ½ h stirring | 208 |
| 1 h stirring | 200 |
| 2 h stirring | 210 |
| 4 h stirring | 190 |
| 6 h stirring | 210 |

Here, the stabilizer content and the contents of 4-(methacryloyloxy)benzophenone, methyl methacrylate and methacrylic acid remained constant within the scope of measurement accuracy.

Example 5

Apparatus: 2 l round-bottom flask with mechanical stirrer, reflux condenser, Pt100 temperature sensor, air inlet tube and electrically heated oil bath.
Mixture:
1 kg of the following solution:
30% of 4-(methacryloyloxy)benzophenone dissolved in 60% methyl methacrylate and 10% methacrylic acid directly from the process analogous to example 1, but with a higher colour index.
100 g of activated carbon rods (from Donau Carbon, Norit 0.8 Supra type)
Procedure:
The mixture was weighed out in full and stirred at 40° C. In the meantime, samples were taken continuously and were filtered by a pleated filter and a syringe filter (PTFE, pore size 0.45 µm).

| Time | Pt—Co colour index |
| --- | --- |
| Beforehand | 335 |
| ½ h stirring | 210 |
| 1 h stirring | 191 |
| 2 h stirring | 200 |
| 4 h stirring | 205 |
| 6 h stirring | 225 |

Here, the stabilizer content and the contents of 4-(methacryloyloxy)benzophenone, methyl methacrylate and methacrylic acid remained constant within the scope of measurement accuracy.

Example 6

Apparatus: 2 l round-bottom flask with mechanical stirrer and reflux condenser.
Mixture:
800 g of the following solution:
30% of 4-(methacryloyloxy)benzophenone dissolved in 60% methyl methacrylate and 10% methacrylic acid directly from the process analogous to example 1, but with a higher colour index.
80 g of activated carbon rods (from Donau Carbon, Norit 0.8 Supra type)

Procedure:

The mixture was weighed out in full, stirred at room temperature for 1 hour and filtered by a pleated filter.

| Time | Pt—Co colour index |
|---|---|
| Beforehand | 350 |
| 1 h stirring | 235 |

The filtered-off activated carbon had 300 ml of methyl methacrylate added to it, was stirred for 10 minutes at room temperature, and subsequently filtered off with suction. 5 g of the dried activated carbon had 50 g of the 4-(methacryloyloxy)benzophenone solution in methyl methacrylate and methacrylic acid added thereto, was stirred for ½ hour at room temperature and filtered by a pleated filter.

| Time | Pt—Co colour index |
|---|---|
| Beforehand | 350 |
| ½ h stirring | 290 |

Example 7

Apparatus: 250 ml glass beaker, magnetic stirrer.
Mixture:
50 g of the following solution:
30% of 4-(methacryloyloxy)benzophenone dissolved in 60% methyl methacrylate and 10% methacrylic acid directly from the process analogous to example 1, but with a higher colour index.
5 g of Tonsil
Procedure:
The mixture was weighed out in full, stirred at room temperature for ½ hour and filtered by a pleated filter.

| Time | Pt—Co colour index |
|---|---|
| Beforehand | 250 |
| ½ h stirring | 200 |

Example 8

Apparatus: see example 1, but with 4 l flask.
Mixture:
4.0 mol of 4-hydroxybenzophenone: 796.0 g
4.4 mol of methacrylic anhydride, (purity 98.65% (GC), methacrylic acetic anhydride 0.62%,
  acetic anhydride not detected;
  stabilized with 1980 ppm of 2,4-dimethyl-6-tert-butylphenol: 694.8 g
0.023 mol of H$_2$SO$_4$, conc., 0.15% of mixture: 2.26 g (1.23 ml) 2,4-dimethyl-6-tert-butylphenol, 1000 ppm of prod.=1065 mg
Neutralization H$_2$SO$_4$: 0.052 mol NaOH=2.08 g dissolved in 10 g H$_2$O Hydrolysis of methacrylic anhydride excess: 25.6 g MeOH (0.80 mol)
Theoretical yield: 1051.7 g
Procedure: The mixture was weighed out in full and then heated to 90° C. with introduction of air. Reaction time: 4 h (conversion check by GC). Cooling was then carried out down to approximately 60° C. and the NaOH dissolved in H$_2$O for neutralization of the H$_2$SO$_4$, and also the MeOH for hydrolysis of the methacrylic anhydride, were added. Stirring was subsequently carried out for 1 h at 60° C., and then the mixture was completely cooled. The mixture was then poured with stirring (metal paddle stirrer, stirring motor) as a thin stream into 3 l of water. After ½ h of stirring, the precipitate was isolated by suction filtration on a glass filter frit, washed again with 2.0 l of H$_2$O (stirred for approximately 30 minutes in a glass beaker with a stirring motor with metal paddle stirrer) and subsequently dried with suction on the suction filter. The solid was subsequently dried to constant mass in air (7 days).
Yield: 1051.7 g=98.7% of theory
Analyses: H$_2$O: 0.06%
2,4-dimethyl-6-tert-butylphenol: 79 ppm
GC: (data after reaction in area % based on the sum of the 4-hydroxybenzophenone derivatives)

| After reaction | After precipitation | |
|---|---|---|
| | 0.007% | methacrylic acid |
| 0.560% | 1.066% | 4-hydroxybenzophenone |
| 0.700% | 1.046% | 4-acetoxybenzophenone |
| 98.740% | 97.142% | 4-(methacryloyloxy)benzophenone |

Example 9

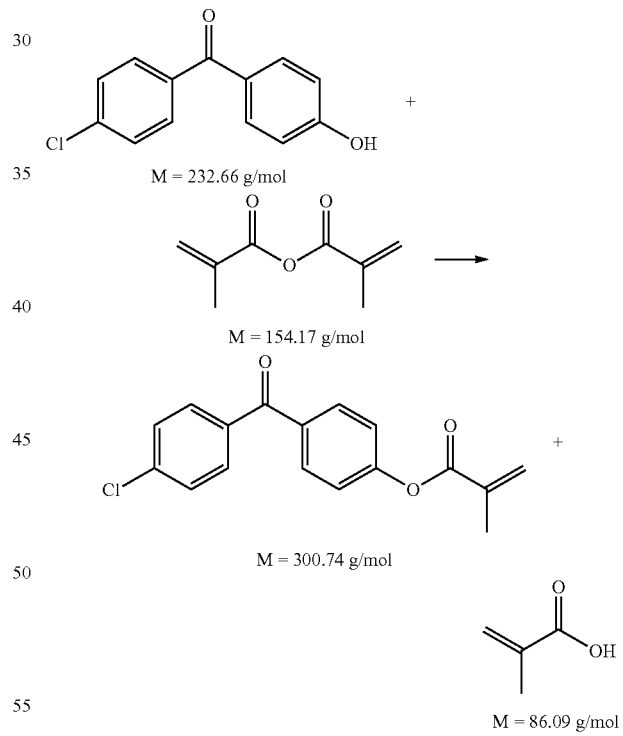

Apparatus: 2 l four-necked round-bottom flask with mechanical stirrer, reflux condenser, Pt100 temperature sensor, air inlet tube and electrically heated oil bath.
Mixture:
0.20 mol of 4-chloro-4'-hydroxybenzophenone: 47.48 g
0.22 mol of MAAH, (purity 97.92% (GC), methacrylic acetic anhydride 1.59%, acetic anhydride not detected;
  stabilized with 2035 ppm of 2,4-dimethyl-6-tert-butylphenol: 35.07 g 0.0013 mol of concentrated sulfuric acid: 0.124 g Total stabilizer content at start of reaction: 1503 ppm based on 4-chloro-4'-hydroxybenzophenone.
Theoretical yield: 60.15 g
Procedure:
The mixture was weighed out in full and then heated to 90° C. with stirring and introduction of air. The reaction time at 90° C. is 4 h. Then the mixture was poured with stirring (metal paddle stirrer, stirring motor) as a thin stream into 0.18 l of water. After 0.5 h of stirring, the precipitate was isolated by suction filtration on a glass filter frit, washed twice again with in each case 0.18 l of water and subsequently dried using air on the suction filter. The solid was subsequently dried in air.
Yield: 56.6 g (94% of theory)
Gas chromatography:
1.344% of 4-chloro-4'-hydroxybenzophenone
1.307% 4-chloro-4'-acetoxpenzophenone
96.17% 4-chloro-4'-(methacryloyloxy)benzophenone Example 10

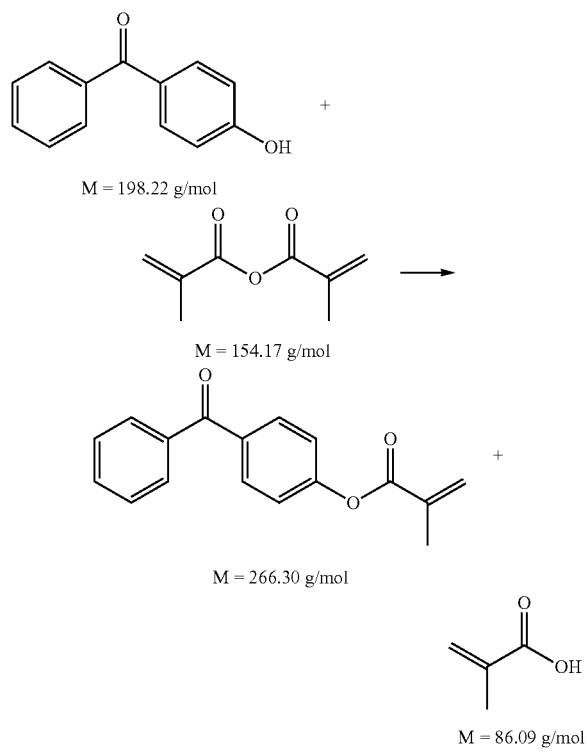

Apparatus: 2 l four-necked round-bottom flask with mechanical stirrer, reflux condenser, Pt100 temperature sensor, air inlet tube and electrically heated oil bath.
Mixture:
1.51 mol of 4-hydroxybenzophenone, 99.8%: 300 g
1.70 mol of MAAH (purity 98.48% (GC), methacrylic acetic anhydride 1.131%, acetic anhydride not detected; stabilized with 1871 ppm of 2,4-dimethyl-6-tert-butylphenol): 262.8 g
1.80 mol of MMA: 180 g
0.0227 mol of NaOH (50% in H$_2$O): 1.816 g
Total stabilizer content at start of reaction: 1639 ppm based on 4-hydroxybenzophenone.

Esterification of the excess methacrylic anhydride with 9.7 g of methanol (0.3 mol) For the preparation of the 30% strength solution in MMA: 600 g of MMA
Theoretical yield: 1354 g
Procedure:
The mixture was weighed out in full and then heated to 90° C. with stirring and introduction of air. The reaction time at 90° C. is 3 h. Cooling was then carried out, down to approximately 60° C., and the sodium hydroxide dissolved in water for neutralization of the catalyst sulfuric acid, and also the methanol for esterification of the unreacted methacrylic anhydride, were added. Stirring was subsequently carried out for 1 h at 60° C., and then 600 g of methyl methacrylate were added to the mixture with stirring. The resulting solution was cooled to room temperature with stirring, and filtered. The solution of 4-(methacryloyloxy)benzophenone in methyl methacrylate has the following composition, determined by gas chromatography (figures in wt %):
59.1% methyl methacrylate
10.5% methacrylic acid
0.32% 4-hydroxybenzophenone
0.46% 4-(acetoxy)benzophenone
29.1% 4-(methacryloyloxy)benzophenone
The water content is 0.10%, the stabilizer content is 203 ppm of 2,4-dimethyl-6-tert-butylphenol.
The Pt—Co colour index is 111 APHA.
Yield: 1347 g (99% of theory)

Example 11

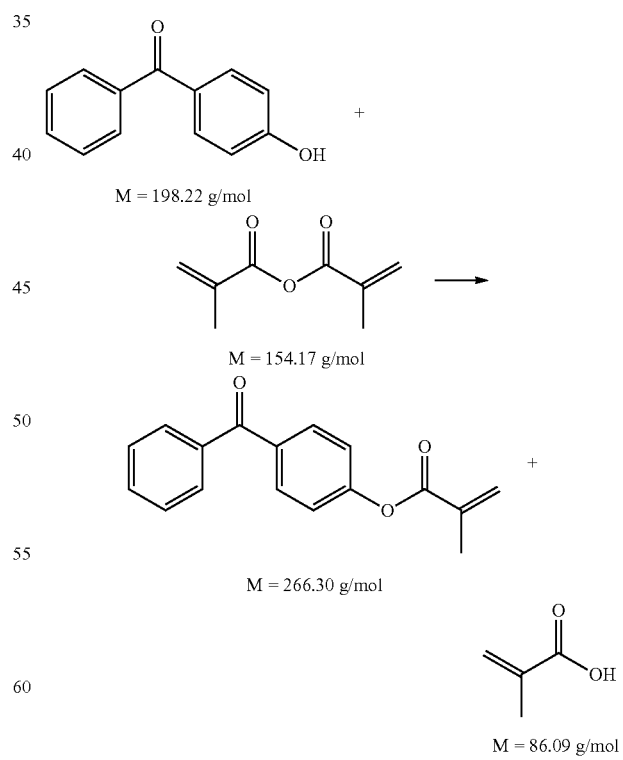

Apparatus: 2 l four-necked round-bottom flask with mechanical stirrer, reflux condenser, Pt100 temperature sensor, air inlet tube, electrically heated oil bath, pressure filter.

Mixture:

1.51 mol of 4-hydroxybenzophenone, 99.8%: 300 g 1.70 mol of MAAH (purity 98.48% (GC), methacrylic acetic anhydride 1.131%, acetic anhydride not detected;

stabilized with 1871 ppm of 2,4-dimethyl-6-tert-butylphenol): 262.8 g 0.30 mol of MMA: 30 g 0.0087 mol of concentrated sulfuric acid: 0.846 g Total stabilizer content at start of reaction: 1639 ppm based on 4-hydroxybenzophenone.

Neutralization of the catalyst acid with 1.57 g of (50% strength) aqueous sodium hydroxide solution Esterification of the excess methacrylic anhydride with 9.7 g of methanol (0.3 mol)

Theoretical yield: 402.1 g

Procedure:

The mixture was weighed out in full and then heated to 90° C. with stirring and introduction of air. The reaction time at 90° C. is 2 h. Cooling was then carried out, down to approximately 60° C., and the sodium hydroxide dissolved in water for neutralization of the catalyst sulfuric acid, and also the methanol for esterification of the unreacted methacrylic anhydride, were added. Stirring was subsequently carried out for 1 h at 60° C., and then 400 g of methylcyclohexane were added to the mixture with stirring. The resulting solution was cooled to room temperature with stirring and the solid which then precipitated out was filtered over a pressure filter. The filter residue was dried in air.

Yield: 278.25 g (69.2% of theory)

Gas Chromatography:

0.032 area % of methyl methacrylate 0.008 area % of methacrylic acid 0.329 area % of 4-hydroxybenzophenone 0.289 area % of 4-(acetoxy)benzophenone 98.71 area % of 4-(methacryloyloxy)benzophenone Example 12

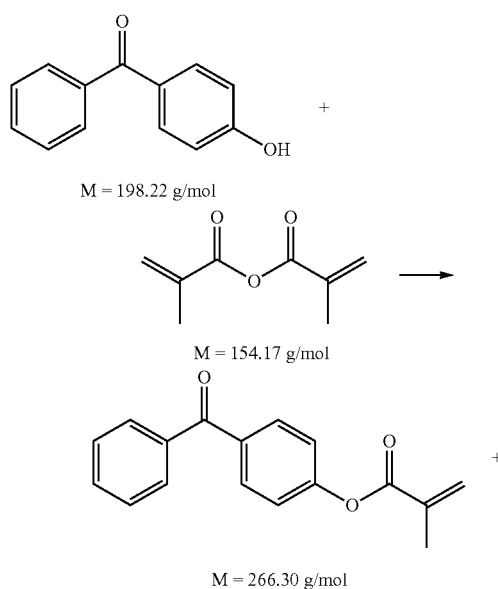

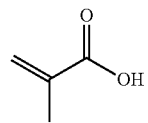

M = 86.09 g/mol

Apparatus: 2 l four-necked round-bottom flask with mechanical stirrer, reflux condenser, Pt100 temperature sensor, air inlet tube and electrically heated oil bath.

Mixture:

1.51 mol of 4-hydroxybenzophenone, 99.7%: 300 g 1.70 mol of MAAH (purity 98.59% (GC), methacrylic acetic anhydride 0.40%, acetic anhydride not detected;

stabilized with 2070 ppm of 2,4-dimethyl-6-tert-butylphenol): 262.8 g 1.80 mol of MMA: 180 g 0.0087 mol of sulfuric acid (50% in H$_2$O): 1.692 g Total stabilizer content at start of reaction: 1813 ppm based on 4-hydroxybenzophenone.

Neutralization of the catalyst acid with 1.8 g of aqueous sodium hydroxide solution dissolved in 10 g of water Esterification of the excess methacrylic anhydride with 22.4 g of methanol Theoretical yield: 1354 g Procedure:

The mixture was weighed out in full and then heated to 90° C. with stirring and introduction of air. The reaction time at 90° C. is 3.5 h. Cooling was then carried out, down to approximately 60° C., and the sodium hydroxide dissolved in water for neutralization of the catalyst sulfuric acid, and also the methanol for esterification of the unreacted methacrylic anhydride, were added. Stirring was subsequently carried out for 1 h at 60° C., and then 600 g of methyl methacrylate were added to the mixture with stirring. The resulting solution was cooled to room temperature with stirring, and filtered. The solution of 4-(methacryloyloxy)benzophenone in methyl methacrylate has the following composition, determined by gas chromatography (figures in wt %):

57.8% methyl methacrylate 10.1% methacrylic acid 0.45% 4-hydroxybenzophenone 0.35% 4-(acetoxy)benzophenone 29.6% 4-(methacryloyloxy)benzophenone The water content is 0.10%, the stabilizer content is 61 ppm of 2,4-dimethyl-6-tert-butylphenol. The Pt—Co colour index is 142 APHA.

Yield: 1346 g (99.4% of theory)

Example 13

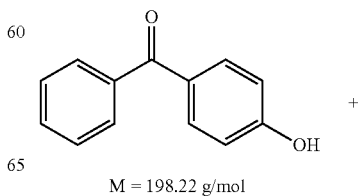

M = 198.22 g/mol

-continued

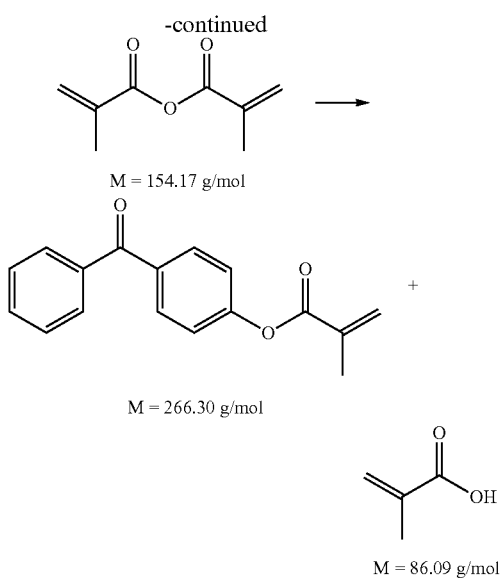

Apparatus: 2 l four-necked round-bottom flask with mechanical stirrer, reflux condenser, Pt100 temperature sensor, air inlet tube and electrically heated oil bath.

Mixture:

1.51 mol of 4-hydroxybenzophenone, 99.7%: 300 g 1.70 mol of MAAH (purity 98.59% (GC), methacrylic acetic anhydride 0.40%,
  acetic anhydride not detected;
  stabilized with 2070 ppm of 2,4-dimethyl-6-tert-butylphenol): 262.8 g 1.80 mol of MMA: 180 g 0.0087 mol of trifluoromethanesulfonic acid: 1.306 g Total stabilizer content at start of reaction: 1813 ppm based on 4-hydroxybenzophenone.

Neutralization of the catalyst acid with 1.8 g of aqueous sodium hydroxide solution dissolved in 10 g of water Esterification of the excess methacrylic anhydride with 22.4 g of methanol.

Theoretical yield: 1354 g

Procedure:

The mixture was weighed out in full and then heated to 90° C. with stirring and introduction of air. The reaction time at 90° C. is 3 h. Cooling was then carried out, down to approximately 60° C., and the sodium hydroxide dissolved in water for neutralization of the catalyst sulfuric acid, and also the methanol for esterification of the unreacted methacrylic anhydride, were added. Stirring was subsequently carried out for 1 h at 60° C., and then 600 g of methyl methacrylate were added to the mixture with stirring. The resulting solution was cooled to room temperature with stirring, and filtered. The solution of 4-(methacryloyloxy)benzophenone in methyl methacrylate has the following composition, determined by gas chromatography (figures in wt %):

57.7% methyl methacrylate
10.2% methacrylic acid
0.41% 4-hydroxybenzophenone
0.43% 4-(acetoxy)benzophenone
29.7% 4-(methacryloyloxy)benzophenone The water content is 0.07%, the stabilizer content is 48 ppm of 2,4-dimethyl-6-tert-butylphenol. The Pt—Co colour index is 158 APHA.

Yield: 1348 g (99.4% of theory)

Example 14

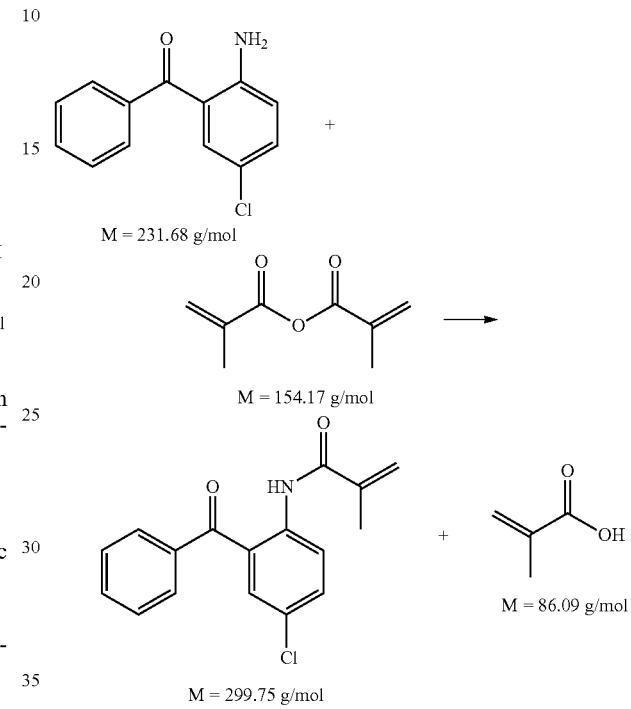

Apparatus: 100 ml three-necked round-bottom flask with magnetic stirrer, reflux condenser, Pt100 temperature sensor, air inlet tube and electrically heated oil bath.

Mixture:

0.05 mol of 2-amino-5-chlorobenzophenone: 11.6 g 0.053 mol of MAAH, (purity 98.51% (GC), methacrylic acetic anhydride 0.20%,
  acetic anhydride not detected;
  stabilized with 2160 ppm of 2,4-dimethyl-6-tert-butylphenol: 8.2 g 0.4 mmol of concentrated sulfuric acid: 0.039 g Total stabilizer content at start of reaction: 1527 ppm based on 2-amino-5-chlorobenzophenone.

Theoretical yield: 15.0 g

Procedure:

The mixture was weighed out in full and then heated to 70° C. with stirring and introduction of air. The reaction time at 70° C. is 4 h. Then the mixture was poured with stirring (metal paddle stirrer, stirring motor) as a thin stream into 0.18 l of water. After 0.5 h of stirring, the precipitate was isolated by suction filtration on a glass filter frit, washed twice again with in each case 0.18 l of water and subsequently dried using air on the suction filter. The solid was subsequently dried in air.

Yield: 14.0 g (93% of theory)

Gas Chromatography:

0.11% of 2-amino-5-chlorobenzophenone 0.32% 2-acetamido-5-chlorobenzophenone 97,835% N-(2-benzoyl-4-chlorophenyl)methacrylamide Comparative Example 1

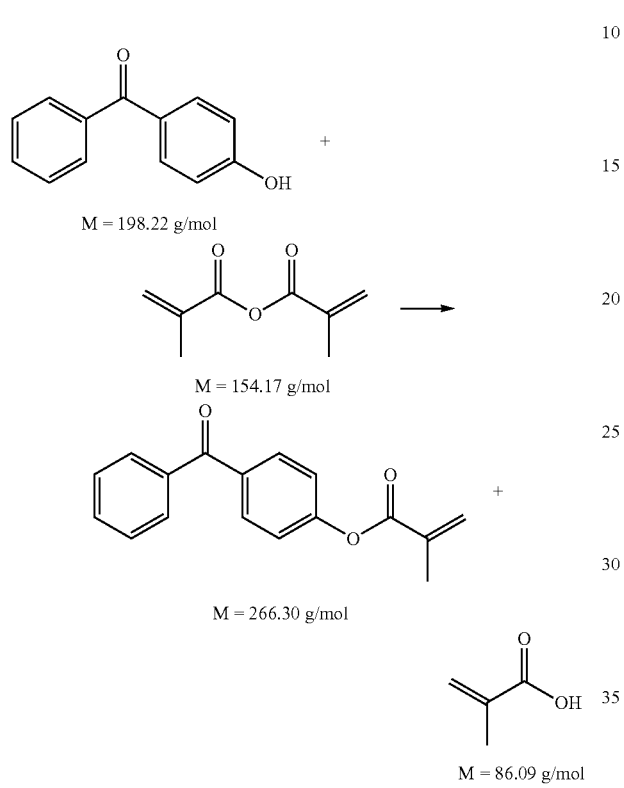

Apparatus: 2 l four-necked round-bottom flask with mechanical stirrer, reflux condenser, Pt100 temperature sensor, air inlet tube and electrically heated oil bath.

Mixture:

1.51 mol of 4-hydroxybenzophenone, 99.7%: 300 g 1.70 mol of MAAH (purity 98.59% (GC), methacrylic acetic anhydride 0.40%, acetic anhydride not detected;

stabilized with 2070 ppm of 2,4-dimethyl-6-tert-butylphenol): 262.8 g 1.80 mol of MMA: 180 g 0.0087 mol of concentrated sulfuric acid: 0.846 g Total stabilizer content at start of reaction: 1813 ppm based on 4-hydroxybenzophenone.

Neutralization of the catalyst acid with 1.57 g of (50% strength) aqueous sodium hydroxide solution Esterification of the excess methacrylic anhydride with 9.7 g of methanol (0.3 mol)

For the preparation of the 30% strength solution in MMA: 600 g of MMA

Theoretical yield: 1354 g

Procedure:

The mixture was weighed out in full and then heated to 90° C. with stirring and introduction of air.

The reaction time at 90° C. is 5 h. The mixture polymerized on subsequent cooling to 60° C.

Yield: —

Comparative Example 2

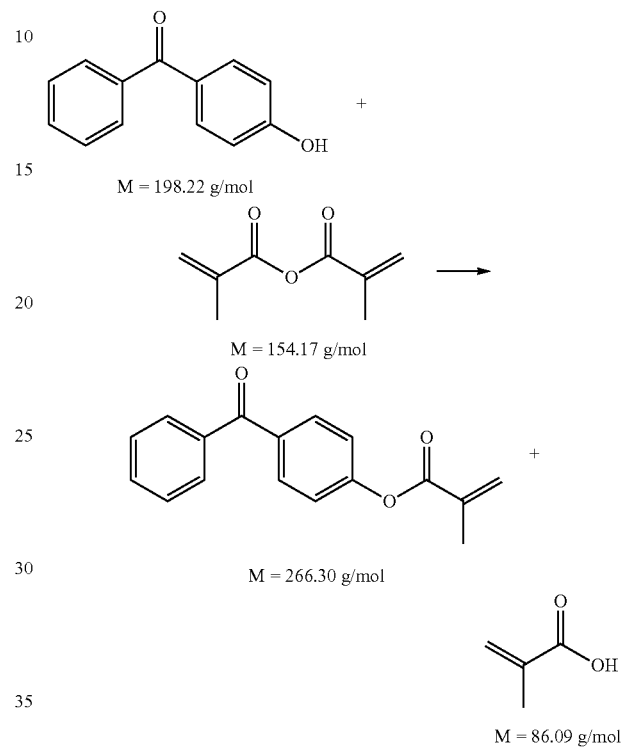

Apparatus: 2 l four-necked round-bottom flask with mechanical stirrer, reflux condenser, Pt100 temperature sensor, air inlet tube and electrically heated oil bath.

Mixture:

1.51 mol of 4-hydroxybenzophenone, 99.7%: 300 g 1.70 mol of MAAH (purity 98.72% (GC), methacrylic acetic anhydride 0.827%, acetic anhydride not detected;

stabilized with 1059 ppm of 2,4-dimethyl-6-tert-butylphenol): 262.8 g 1.80 mol of MMA: 180 g 0.0087 mol of concentrated sulfuric acid: 0.846 g 273 mg of 2,4-dimethyl-6-tert-butylphenol Total stabilizer content at start of reaction: 1835 ppm based on 4-hydroxybenzophenone.

Neutralization of the catalyst acid with 1.57 g of (50% strength) aqueous sodium hydroxide solution Esterification of the excess methacrylic anhydride with 9.7 g of methanol (0.3 mol) For the preparation of the 30% strength solution in MMA: 600 g of MMA Theoretical yield: 1354 g Procedure:

The mixture was weighed out in full and then heated to 90° C. with stirring and introduction of air. The reaction time at 90° C. is 5.5 h. After 5 h of reaction time, a sample was taken and worked up separately (cooling to 60° C., neutralization with aqueous sodium hydroxide solution, reaction with MeOH, dilution with MMA). After 5.5 h, the mixture polymerized.

Yield: —

Analyses: After work-up, the sample after 5 h reaction time showed a colour index of 600 APHA and also a stabilizer content of 9 ppm of 2,4-dimethyl-6-tert-butylphenol.

Comparative Example 3

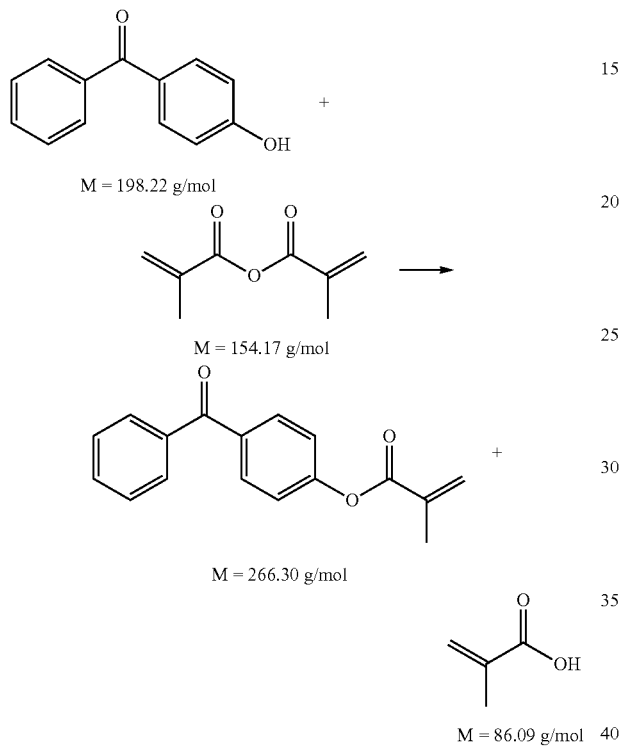

Apparatus: 2 l four-necked round-bottom flask with mechanical stirrer, reflux condenser, Pt100 temperature sensor, air inlet tube and electrically heated oil bath.

Mixture:
1.51 mol of 4-hydroxybenzophenone, 99.8%: 300 g
1.70 mol of MAAH (purity 82.63% (GC), methacrylic acetic anhydride 1.668%,
    acetic anhydride not detected;
    stabilized with 2870 ppm of 2,4-dimethyl-6-tert-butylphenol): 262.8 g
1.80 mol of MMA: 180 g
0.0087 mol of concentrated sulfuric acid: 0.846 g
Total stabilizer content at start of reaction: 2514 ppm based on 4-hydroxybenzophenone.

Neutralization of the catalyst acid with 1.57 g of (50% strength) aqueous sodium hydroxide solution Esterification of the excess methacrylic anhydride with 9.7 g of methanol (0.3 mol) For the preparation of the 30% strength solution in MMA: 600 g of MMA Theoretical yield: 1354 g Procedure:

The mixture was weighed out in full and then heated to 90° C. with stirring and introduction of air.

The reaction time at 90° C. is 6 h. Cooling was then carried out, down to approximately 60° C., and the sodium hydroxide dissolved in water for neutralization of the catalyst sulfuric acid, and also the methanol for esterification of the unreacted methacrylic anhydride, were added. Stirring was subsequently carried out for 1 h at 60° C., and then 600 g of methyl methacrylate were added to the mixture with stirring. The resulting solution was cooled to room temperature with stirring, and filtered. The solution of 4-(methacryloyloxy)benzophenone in methyl methacrylate has the following composition, determined by gas chromatography (figures in wt %):

60.3% methyl methacrylate
9.1% methacrylic acid
2.35% 4-hydroxybenzophenone
1.06% 4-(acetoxy)benzophenone
25.5% 4-(methacryloyloxy)benzophenone The water content is 0.11%, the stabilizer content is 330 ppm of 2,4-dimethyl-6-tert-butylphenol. The Pt—Co colour index is 147 APHA. Thus, the content of the unreacted keto-functionalized aromatic phenol relative to the content of keto-functionalized aromatic methacrylate is high enough that in application significant amounts can migrate or negatively influence the properties of the polymer.

Yield: 1346 g (99% of theory)

Comparative Example 4

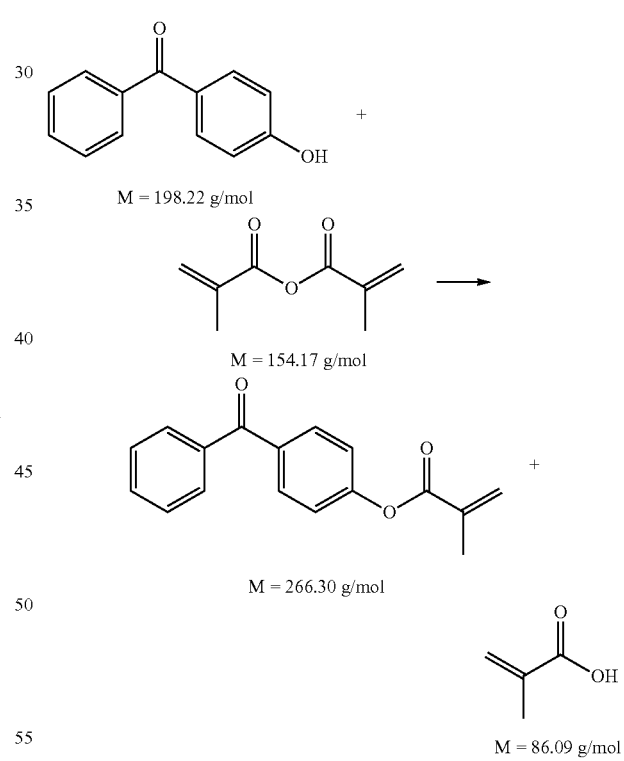

Apparatus: 2 l four-necked round-bottom flask with mechanical stirrer, reflux condenser, Pt100 temperature sensor, air inlet tube and electrically heated oil bath.

Mixture:
1.51 mol of 4-hydroxybenzophenone, 99.8%: 300 g
1.70 mol of MAAH (purity 86.86% (GC), methacrylic acetic anhydride 4.96%,
    acetic anhydride not detected;
    stabilized with 1270 ppm of 2,4-dimethyl-6-tert-butylphenol): 262.8 g 1.80 mol of MMA: 180 g
0.0087 mol of concentrated sulfuric acid: 0.846 g
117 mg of 2,4-dimethyl-6-tert-butylphenol
Total stabilizer content at start of reaction: 1502 ppm based on 4-hydroxybenzophenone.

Neutralization of the catalyst acid with 1.57 g of (50% strength) aqueous sodium hydroxide solution Esterification of the excess methacrylic anhydride with 9.7 g of methanol (0.3 mol) For the preparation of the 30% strength solution in MMA: 600 g of MMA Theoretical yield: 1354 g Procedure:

The mixture was weighed out in full and then heated to 90° C. with stirring and introduction of air. The reaction time at 90° C. is 6 h. Cooling was then carried out, down to approximately 60° C., and the sodium hydroxide dissolved in water for neutralization of the catalyst sulfuric acid, and also the methanol for esterification of the unreacted methacrylic anhydride, were added. Stirring was subsequently carried out for 1 h at 60° C., and then 600 g of methyl methacrylate were added to the mixture with stirring. The resulting solution was cooled to room temperature with stirring, and filtered. The solution of 4-(methacryloyloxy)benzophenone in methyl methacrylate has the following composition, determined by gas chromatography (figures in wt %):

59.4% methyl methacrylate
11.4% methacrylic acid
0.79% 4-hydroxybenzophenone
2.83% 4-(acetoxy)benzophenone
26.0% 4-(methacryloyloxy)benzophenone The water content is 0.08%, the stabilizer content is 140 ppm of 2,4-dimethyl-6-tert-butylphenol. The Pt—Co colour index is 165 APHA. Thus, the content of the acetylated keto-functionalized aromatic phenol relative to the content of keto-functionalized aromatic methacrylate is high enough that in application significant amounts can migrate or negatively influence the properties of the polymer.

Yield: 1351 g (99% of theory)

Comparative Example 5

$M = 198.22$ g/mol $M = 154.17$ g/mol $M = 266.30$ g/mol

-continued $M = 86.09$ g/mol

Apparatus: 2 l four-necked round-bottom flask with mechanical stirrer, reflux condenser, Pt100 temperature sensor, air inlet tube and electrically heated oil bath.

Mixture:
1.51 mol of 4-hydroxybenzophenone, 99.8%: 300 g
1.70 mol of MAAH (purity 86.86% (GC), methacrylic acetic anhydride 4.96%,
acetic anhydride not detected;
stabilized with 1270 ppm of 2,4-dimethyl-6-tert-butylphenol): 262.8 g
1.80 mol of MMA: 180 g
0.0087 mol of concentrated sulfuric acid: 0.846 g
117 mg of 2,4-dimethyl-6-tert-butylphenol
Total stabilizer content at start of reaction: 1502 ppm based on 4-hydroxybenzophenone.

Neutralization of the catalyst acid with 1.57 g of (50% strength) aqueous sodium hydroxide solution Esterification of the excess methacrylic anhydride with 9.7 g of methanol (0.3 mol) For the preparation of the 30% strength solution in MMA: 600 g of MMA Theoretical yield: 1354 g Procedure:

The mixture was weighed out in full and then heated to 90° C. with stirring and introduction of air. The reaction time at 90° C. is 2 h. Cooling was then carried out, down to approximately 60° C., and the sodium hydroxide dissolved in water for neutralization of the catalyst sulfuric acid, and also the methanol for esterification of the unreacted methacrylic anhydride, were added. Stirring was subsequently carried out for 1 h at 60° C., and then 600 g of methyl methacrylate were added to the mixture with stirring. The resulting solution was cooled to room temperature with stirring, and filtered. The solution of 4-(methacryloyloxy)benzophenone in methyl methacrylate has the following composition, determined by gas chromatography (figures in wt %):

59.6% methyl methacrylate
11.0% methacrylic acid
2.53% 4-hydroxybenzophenone
2.62% 4-(acetoxy)benzophenone
24.1% 4-(methacryloyloxy)benzophenone The water content is 0.09%, the stabilizer content is 178 ppm of 2,4-dimethyl-6-tert-butylphenol. The Pt—Co colour index is 126 APHA. Thus, the content of the unreacted and also of the acetylated keto-functionalized aromatic phenol relative to the content of keto-functionalized aromatic methacrylate is high enough that in application significant amounts can migrate or negatively influence the properties of the polymer.

Yield: 1348 g (99% of theory)

The invention claimed is:

1. A method for the preparation of a keto-functionalized aromatic (meth)acrylate, comprising reacting a keto-functionalized aromatic alcohol or a keto-functionalized aromatic amine with (meth)acrylic anhydride in the presence of a catalyst, wherein the catalyst is an acid with a $pK_a$ of <2 or a base with a $pK_b$ of <9, in which reactants, products formed and catalyst are present together in a reaction matrix at a reaction temperature of between 50° C. and 120° C., and wherein:
   a) the reactants, products formed and catalyst have a residence time in the reaction matrix that is restricted to from 0.1 to, at most, 4 hours; and
   b) the (meth)acrylic anhydride used comprises a content of (meth)acrylic acetic anhydride of <4.5%.

2. The method of claim 1, wherein the keto-functionalized aromatic alcohol or the keto-functionalized aromatic amine has its keto function adjacent to the aromatic system.

3. The method of claim 1, wherein the keto-functionalized aromatic alcohol or the keto-functionalized aromatic amine comprises either a free $NH_2$ or a free OH group on its aromatic system.

4. The method of claim 1, wherein the keto-functionalized aromatic (meth)acrylate is precipitated by addition of water or of an organic solvent into the reaction mixture and is isolated in solid form by filtration.

5. The method of claim 1, wherein the keto-functionalized aromatic alcohol or the keto-functionalized aromatic amine comprises either a free $NH_2$ or a free OH group linked via a spacer unit to its aromatic system.

6. The method of claim 5, wherein the spacer unit is, or comprises, an oligoether, alkyl, aryl, ether, thioether, amine, ester, thioester, or amide.

7. The method of claim 1, wherein the reaction matrix further comprises a stabilizer at the start of the reaction and the stabilizer is present at a concentration of between greater than 0 and 5000 ppm based on the keto-functionalized aromatic alcohols or amines used.

8. The method of claim 1, wherein the (meth)acrylic anhydride used has a purity of >93% and the reaction has a duration of 1 to 3 hours.

9. The method of claim 1, wherein: a) said catalyst is an acid and, after the reaction is complete, the catalyst is neutralized with a base; and b) after neutralization, the Pt—Co colour index is, or is adjusted to <500 APHA, measured as a 30 wt % solution of the keto-functionalized aromatic (meth)acrylate in 60 wt % methyl methacrylate and 10 wt % methacrylic acid.

10. The method of claim 1, wherein the product is treated with an adsorbent and, after the treatment, the adsorbent is removed to give a product with a Pt—Co colour index of <500 APHA measured as a 30 wt % solution of the keto-functionalized aromatic (meth)acrylate in 60 wt % methyl methacrylate and 10 wt % methacrylic acid.

11. The method of claim 1, wherein the reaction is interrupted at a conversion of >90% of the keto-functionalized aromatic alcohol or keto-functionalized aromatic amine.

12. The method of claim 1, wherein the reaction is carried out in the presence of catalytic amounts of acid.

13. The method of claim 12, wherein said acid is sulfuric acid, alkylsulfonic acid or arylsulfonic acid.

14. The method of claim 12, wherein, after the reaction, the catalytic amounts of acid are neutralized with an aqueous base.

15. The method of claim 14, wherein the aqueous base is an aqueous alkali metal hydroxide solution or ammonia solution.

16. The method of claim 1, wherein the reaction is carried out over 1-3 hours at 60 to 95° C.

17. The method of claim 1, further comprising addition of a liquid (meth)acrylic ester or styrene into the reaction mixture at the end of the reaction.

18. The method of claim 3, wherein the keto-functionalized aromatic (meth)acrylate is precipitated by addition of water or of an organic solvent into the reaction mixture and is isolated in solid form by filtration.

19. The method of claim 18, wherein: a) said catalyst is an acid and, after the reaction is complete, the catalyst is neutralized with a base; and b) after neutralization, the Pt—Co colour index is, or is adjusted to <500 APHA, measured as a 30 wt % solution of the keto-functionalized aromatic (meth)acrylate in 60 wt % methyl methacrylate and 10 wt % methacrylic acid.

20. The method of claim 1, wherein (meth)acrylic anhydride is reacted with 4-hydroxybenzophenone and at the end of the reaction, and prior to processing, there is 0.723% or less of 4-(acetoxy)benzophenone in the product.

21. The method of claim 1, wherein the reaction is carried out in the presence of catalytic amounts of aqueous sodium hydroxide solution.

22. The method of claim 1, wherein the keto-functionalized aromatic alcohol is 4-hydroxybenzophenone or 4-chloro-4'-hydroxybenzophenone; and the keto-functionalized aromatic amine is 2-amino-5-chlorobenzophenone.

* * * * *